(12) United States Patent
McLaughlin et al.

(10) Patent No.: US 9,808,349 B2
(45) Date of Patent: Nov. 7, 2017

(54) EXPANDABLE VERTEBRAL IMPLANT

(75) Inventors: Colm McLaughlin, Philadelphia, PA (US); Jason Gray, East Greenville, PA (US); James Himmelberger, Souderton, PA (US)

(73) Assignee: Globus Medical Inc, Audubon, PA (US)

( * ) Notice: Subject to any disclaimer, the term of this patent is extended or adjusted under 35 U.S.C. 154(b) by 0 days.

(21) Appl. No.: 13/606,625

(22) Filed: Sep. 7, 2012

(65) Prior Publication Data

US 2012/0330426 A1 Dec. 27, 2012

Related U.S. Application Data

(63) Continuation of application No. 12/758,529, filed on Apr. 12, 2010, now Pat. No. 8,282,683.

(51) Int. Cl.
*A61F 2/44* (2006.01)
*A61F 2/46* (2006.01)
*A61F 2/30* (2006.01)

(52) U.S. Cl.
CPC .............. *A61F 2/44* (2013.01); *A61F 2/4455* (2013.01); *A61F 2/4611* (2013.01); *A61F 2/4465* (2013.01); *A61F 2002/3008* (2013.01); *A61F 2002/3055* (2013.01); *A61F 2002/30383* (2013.01); *A61F 2002/30393* (2013.01); *A61F 2002/30395* (2013.01); *A61F 2002/30477* (2013.01); *A61F 2002/30495* (2013.01); *A61F 2002/30504* (2013.01); *A61F 2002/30505* (2013.01); *A61F 2002/30512* (2013.01); *A61F 2002/30523* (2013.01); *A61F 2002/30571* (2013.01); *A61F 2002/30578* (2013.01); *A61F 2002/30579* (2013.01); *A61F 2002/30601* (2013.01); *A61F 2002/30604* (2013.01); *A61F 2002/30828* (2013.01); *A61F 2002/30843* (2013.01); *A61F 2002/30846* (2013.01); *A61F 2002/4475* (2013.01); *A61F 2002/4625* (2013.01); *A61F 2002/4627* (2013.01); *A61F 2002/4629* (2013.01);

(Continued)

(58) Field of Classification Search
CPC .. A61F 2002/30578; A61F 2002/30514; A61F 2002/30517; A61F 2002/30507; A61F 2/44; A61F 2/4455–2/46
USPC ...... 623/17.11–17.16; 403/43, 44, 46, 109.1, 403/109.4, 109.8
See application file for complete search history.

(56) References Cited

U.S. PATENT DOCUMENTS 3,741,251 A 6/1973 Rees
4,126,338 A 11/1978 Coel et al.
(Continued)

*Primary Examiner* — Jacqueline Johanas

(57) ABSTRACT

The present invention relates to an expandable implant for engagement between vertebrae generally comprising an inner member, outer member, and gear member positioned coaxial with respect to each other such that the inner and outer members are moveable relative to each other along an axis. The gear member is axially fixed to the outer member and freely rotatable with respect to the outer member and the gear member threadedly engages a threaded portion of the inner member to translate inner member along the axis. The implant is configured to engage the vertebrae in a predetermined alignment and the gear member includes gear teeth exposed to the exterior and configured to be accessible by a tool member at a plurality of angular positions around the perimeter of the implant device.

19 Claims, 7 Drawing Sheets

(52) U.S. Cl.
CPC ............... *A61F 2310/00011* (2013.01); *A61F 2310/00023* (2013.01); *A61F 2310/00131* (2013.01)

(56) References Cited

U.S. PATENT DOCUMENTS

| | | | |
|---|---|---|---|
| 4,341,482 A | 7/1982 | Wollensak | |
| 4,792,320 A | 12/1988 | Nickel | |
| 4,892,546 A * | 1/1990 | Kotz et al. | 623/23.45 |
| 5,234,378 A | 8/1993 | Helgesen et al. | |
| 5,496,216 A | 3/1996 | Rohrle et al. | |
| 5,601,493 A | 2/1997 | Nakazono et al. | |
| 6,010,290 A | 1/2000 | Slesinski et al. | |
| 6,152,927 A * | 11/2000 | Farris | A61B 17/7059 606/287 |
| 6,193,721 B1 * | 2/2001 | Michelson | A61B 17/1604 606/246 |
| 6,306,139 B1 * | 10/2001 | Fuentes | A61B 17/1728 606/295 |
| 6,344,057 B1 | 2/2002 | Rabbe | |
| 6,730,088 B2 * | 5/2004 | Yeh | 606/247 |
| 6,749,386 B2 | 6/2004 | Harris | |
| 6,808,538 B2 * | 10/2004 | Paponneau | 623/17.16 |
| 6,835,159 B2 | 12/2004 | Gehring et al. | |
| 6,976,816 B2 | 12/2005 | Slesinski et al. | |
| 7,056,343 B2 | 6/2006 | Schafer et al. | |
| 7,544,208 B1 | 6/2009 | Mueller et al. | |
| 7,662,182 B2 * | 2/2010 | Zubok et al. | 623/17.11 |
| 7,674,296 B2 * | 3/2010 | Rhoda et al. | 623/17.15 |
| 7,879,096 B2 * | 2/2011 | Dickson et al. | 623/17.11 |
| 8,152,851 B2 * | 4/2012 | Mueller et al. | 623/17.15 |
| 8,161,619 B2 | 4/2012 | Wanthal | |
| 8,211,148 B2 * | 7/2012 | Zhang et al. | 606/257 |
| 8,282,683 B2 * | 10/2012 | McLaughlin et al. | 623/17.11 |
| 8,430,759 B2 | 4/2013 | Wanthal | |
| 8,540,774 B2 * | 9/2013 | Kueenzi et al. | 623/17.16 |
| 8,652,182 B1 * | 2/2014 | Walker | 606/295 |
| 8,721,723 B2 | 5/2014 | Hansell et al. | |
| 2003/0135213 A1 * | 7/2003 | LeHuec | A61B 17/1671 606/86 B |
| 2003/0176925 A1 * | 9/2003 | Paponneau | 623/17.16 |
| 2004/0172129 A1 | 9/2004 | Schafer et al. | |
| 2004/0193272 A1 | 9/2004 | Zubok et al. | |
| 2005/0027293 A1 * | 2/2005 | LeHuec | A61B 17/1671 623/17.11 |
| 2005/0154459 A1 * | 7/2005 | Wolek et al. | 623/17.11 |
| 2005/0281613 A1 | 12/2005 | Tella et al. | |
| 2006/0030851 A1 * | 2/2006 | Bray et al. | 606/69 |
| 2006/0058877 A1 * | 3/2006 | Gutlin et al. | 623/17.11 |
| 2006/0085071 A1 * | 4/2006 | Lechmann et al. | 623/17.11 |
| 2006/0100710 A1 * | 5/2006 | Gutlin et al. | 623/17.15 |
| 2006/0241762 A1 | 10/2006 | Kraus | |
| 2006/0241770 A1 * | 10/2006 | Rhoda et al. | 623/17.15 |
| 2007/0028710 A1 | 2/2007 | Kraus et al. | |
| 2007/0050030 A1 * | 3/2007 | Kim | 623/17.11 |
| 2007/0106384 A1 * | 5/2007 | Bray et al. | 623/17.11 |
| 2007/0191954 A1 | 8/2007 | Hansell et al. | 623/17.15 |
| 2007/0255407 A1 * | 11/2007 | Castleman et al. | 623/17.11 |
| 2007/0255410 A1 * | 11/2007 | Dickson et al. | 623/17.11 |
| 2008/0269806 A1 * | 10/2008 | Zhang et al. | 606/286 |
| 2008/0281424 A1 * | 11/2008 | Parry et al. | 623/17.16 |
| 2009/0043393 A1 | 2/2009 | Duggal et al. | |
| 2009/0088808 A1 * | 4/2009 | Lindemann et al. | 606/289 |
| 2009/0088853 A1 | 4/2009 | Ogilvie et al. | |
| 2009/0105831 A1 * | 4/2009 | Jones et al. | 623/17.16 |
| 2009/0112320 A1 * | 4/2009 | Kraus | 623/17.11 |
| 2009/0138089 A1 * | 5/2009 | Doubler et al. | 623/17.16 |
| 2009/0164017 A1 | 6/2009 | Sommerich | |
| 2009/0164019 A1 | 6/2009 | Hsu et al. | |
| 2009/0210062 A1 * | 8/2009 | Thalgott et al. | 623/17.16 |
| 2010/0070029 A1 | 3/2010 | Drews et al. | |
| 2010/0094424 A1 * | 4/2010 | Woodburn et al. | 623/17.16 |
| 2010/0100186 A1 * | 4/2010 | Zubok et al. | 623/17.16 |
| 2010/0106251 A1 | 4/2010 | Kast | |
| 2010/0179655 A1 * | 7/2010 | Hansell et al. | 623/17.11 |
| 2010/0185297 A1 | 7/2010 | Steinberg | |
| 2010/0274357 A1 * | 10/2010 | Miller et al. | 623/17.16 |
| 2010/0286787 A1 | 11/2010 | Villiers | |
| 2011/0087328 A1 * | 4/2011 | Dickson et al. | 623/17.11 |
| 2011/0097174 A1 | 4/2011 | Varden | |
| 2011/0184424 A1 | 7/2011 | Isch et al. | |
| 2011/0218631 A1 | 9/2011 | Woodburn, Sr. et al. | |
| 2011/0251692 A1 | 10/2011 | McLaughlin | |
| 2011/0257750 A1 * | 10/2011 | Barrall | 623/17.16 |
| 2012/0130493 A1 * | 5/2012 | McLaughlin et al. | 623/17.16 |
| 2012/0209384 A1 | 8/2012 | Arnold et al. | |
| 2012/0265303 A1 | 10/2012 | Refai et al. | |

* cited by examiner

EXPANDABLE VERTEBRAL IMPLANT

CROSS-REFERENCE TO RELATED APPLICATIONS

The present application is a continuation of U.S. patent application Ser. No. 12/758,529, entitled "Expandable Vertebral Implant," filed on Apr. 12, 2010, now U.S. Pat. No. 8,282,683 the entire disclosure of which is incorporated herein by reference.

FIELD OF THE INVENTION

The present invention relates to a device to support the spine after removal of at least a part of a vertebra.

BACKGROUND OF THE INVENTION

When a vertebra is damaged or diseased, surgery may be used to replace the vertebra or a portion thereof with a prosthetic device to restore spinal column support. For example, vertebral body replacement is commonly required in the treatment of vertebral fracture, tumor, or infection.

In recent years, several artificial materials and implants have been developed to replace the vertebral body, such as, for example, titanium cages, ceramic, ceramic/glass, plastic or PEEK, and carbon fiber spacers. Recently, various expandable prosthetics or expandable cages have been developed and used for vertebral body replacement. The expandable prosthetic devices are generally adjustable to the size of the cavity created by a corpectomy procedure and typically are at least partially hollow to accommodate bone cement or bone fragments to facilitate fusion in vivo. Some expandable implants may be adjusted prior to insertion into the cavity, while others may be adjusted in situ. Two advantages of the vertebral body replacement using an expandable prosthetic device that is adjustable in situ is that it is easy to place or insert and it permits an optimal, tight fit and correction of the deformity by in vivo expansion of the device. Some other advantages offered by an expandable prosthetic device are that they can facilitate distraction across the resected vertebral defect for correction of the deformity, and allow immediate load bearing after corpectomy.

Instrumentation and specialized tools for insertion of a vertebral implant is one important design parameter to consider when designing a vertebral implant. Spinal surgery procedures can present several challenges because of the small clearances around the prosthetic when it is being inserted into position. Another important design consideration includes the ability of the device to accommodate various surgical approaches for insertion of the vertebral implant.

SUMMARY OF THE INVENTION

The present invention relates to an expandable prosthetic implant device for engagement between vertebrae generally comprising an inner member, outer member, and gear member positioned coaxial with respect to each other such that the inner and outer members are moveable relative to each other along an axis. The inner member has a hollow interior portion and a threaded external portion and includes a first end portion configured to engage an endplate which is capable of engaging a first vertebral body. The outer member has a hollow interior portion configured to receive the inner member and includes a second end portion configured to engage an endplate which is capable of engaging a second vertebral body. The gear member is axially fixed to the outer member and freely rotatable with respect to the outer member and the gear member threadedly engages the threaded portion of the inner member.

The implant is configured to engage the vertebrae such that first and second end portions are oriented in a predetermined alignment with respect to the first and second vertebral bodies. The gear member includes teeth extending around the perimeter of the gear member and the teeth are exposed to the exterior and configured to be accessible by a tool member.

BRIEF DESCRIPTION OF THE DRAWINGS

The present invention will be more readily understood with reference to the embodiments thereof illustrated in the attached drawing figures, in which.

Throughout the drawing figures, it should be understood that like numerals refer to like features and structures.

DETAILED DESCRIPTION OF THE PREFERRED EMBODIMENTS

Figure 1:
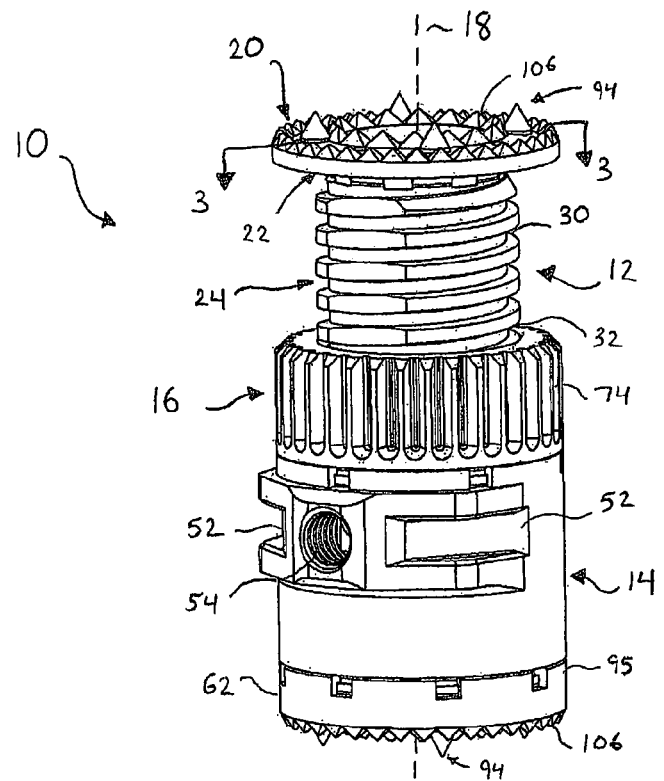
FIG. 1 is a perspective view of an implant in accordance with an embodiment of the present invention.

The preferred embodiments of the invention will now be described with reference to the attached drawing figures. The following detailed description of the invention is not intended to be illustrative of all embodiments. In describing preferred embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Referring to FIGS. 1-6, a preferred embodiment of an expandable vertebral implant 10 is shown. The implant 10 preferably comprises an inner member 12 which may be telescopingly received within an outer member 14. The implant 10 further comprises a gear member 16 generally configured to effect translation of the inner member 12 with respect to the outer member 14 thereby allowing for expansion and contraction of the implant 10. The inner member 12, the outer member 14, and the gear member 16 are preferably centered along a longitudinal axis 18 and define a hollow interior portion which may be filled with bone material, bone growth factors, bone morphogenic proteins, or other materials for encouraging bone growth, blood vessel growth or growth of other tissue through the many apertures in the device. In one preferred embodiment, members 12, 14, and 16 are made of a polyether ether ketone (PEEK) plastic material. There are several known advantages of PEEK plastic material including being radiolucent, having a mechanical strength that is close to bone, and may be more easily sterilized than other plastics. In alternate preferred embodiments, the members 12, 14, and 16 may be made of a biologically inert metal alloys, such as titanium, or other suitable materials.

Referring to FIGS. 1-5, the inner member 12 has a generally cylindrical body 24 with a distal end 22 and a proximal end 36. In a preferred embodiment, the body 24 of the inner member 12 comprises an inner surface 28 and an outer surface 30 and generally defines a hollow interior portion 23 extending axially therethrough. At least part of the outer surface 30 preferably includes external threads 32. Located proximate to the distal end 22 of the body 24 are a plurality of tabs 38 which assist in connecting and positionally locating an endplate 20. In a preferred embodiment, the body 24 is configured and dimensioned to be cooperatively received within outer member 14.

Figure 5:
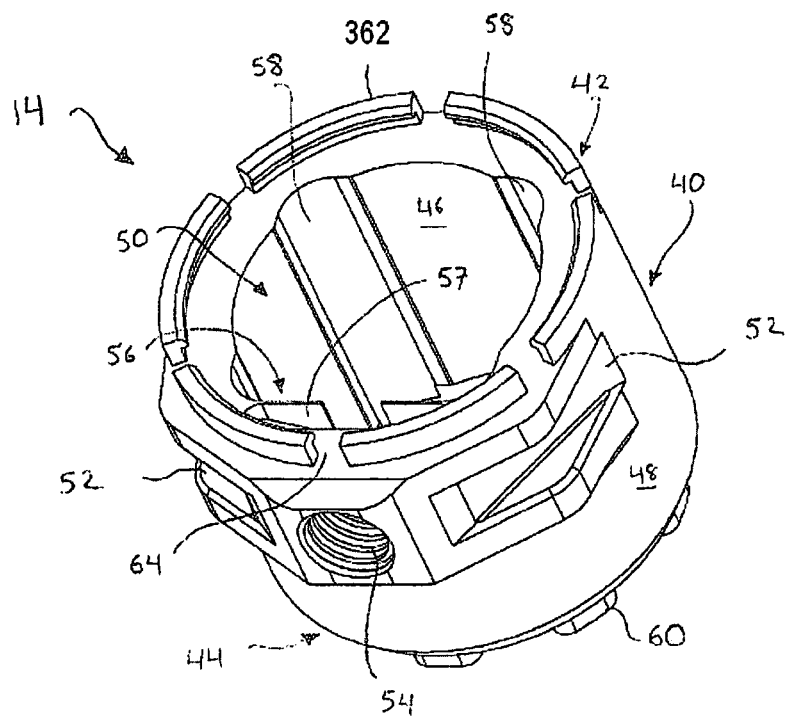
FIG. 5 is perspective view of an embodiment of an outer member of the implant of FIG. 1.

The outer member 14 has a generally cylindrical body 40 with a distal end 42 and a proximal end 44. In a preferred embodiment, the body 40 of the outer member 14 comprises an inner surface 46 and an outer surface 48 and generally defines a hollow interior portion 50 extending axially therethrough. The outer surface 48 preferably has at least one slot 52 and an opening 54 configured and dimensioned to receive a portion of an implantation tool. In a preferred embodiment, the opening 54 extends from the outer surface 48 to the hollow interior portion 50 and at least a portion of the opening 54 is threaded. As best seen in FIG. 5, the inner surface 46 includes a channel 57 for receiving a locking member (discussed below). Located proximate to the proximal end 44 of the outer member 14 are a plurality of tabs 60 which assist in connecting and positionally locating an endplate 62. In a preferred embodiment, a lip 362 is formed around the exterior of the distal end 42 of body 40 and is configured to cooperatively fit with a portion of the gear member 16. A plurality of relief spaces or slots 64 are radially spaced around lip 362 to facilitate a snapping engagement of the lip 362 with the gear member 16. In this regard, slots 64 allow the lip 362 to deform slightly and contract in the radial direction to accommodate gear member 16 to snap on to lip 362. In a preferred embodiment, the interior portion 50 of body 44 is configured and dimensioned to cooperatively receive body 24 of inner member 12 within outer member 14. In this regard, the dimensions of interior portion 50 of body 44 are greater than dimensions of body 24 of inner member 12.

As best seen in FIGS. 2-5, in a preferred embodiment of a prosthetic device 10, the body 24 of the inner member 12 includes a flattened portion 34 which extends at least in part from the distal end 22 to the proximal end 36 and includes a base member 37 having at least one lobe 39 located proximate to the distal end 36 of the body 24. Focusing on FIG. 5, the body 40 of the outer member 14 includes a flattened area 56 and at least one depression 58 on the inner surface 46. When the inner member 12 is assembled within the outer member 14, the flattened area 56 of the outer member 14 cooperatively aligns with the flattened portion 34 of the inner member 12 and the at least one depression 58 of outer member 14 receives the at least one lobe 39 of the inner member 12. The flattened portion 34 and the flattened area 56 along with the lobes 39 and the depressions 58 cooperate to allow the inner member 12 to linearly move with respect to the outer member 14 but prevent the inner member 12 from rotating with respect to the outer member 14. In addition, the base member 37 serves as a stop preventing the inner member 12 from rotating to a point of disengagement from outer member 14.

Figure 6:
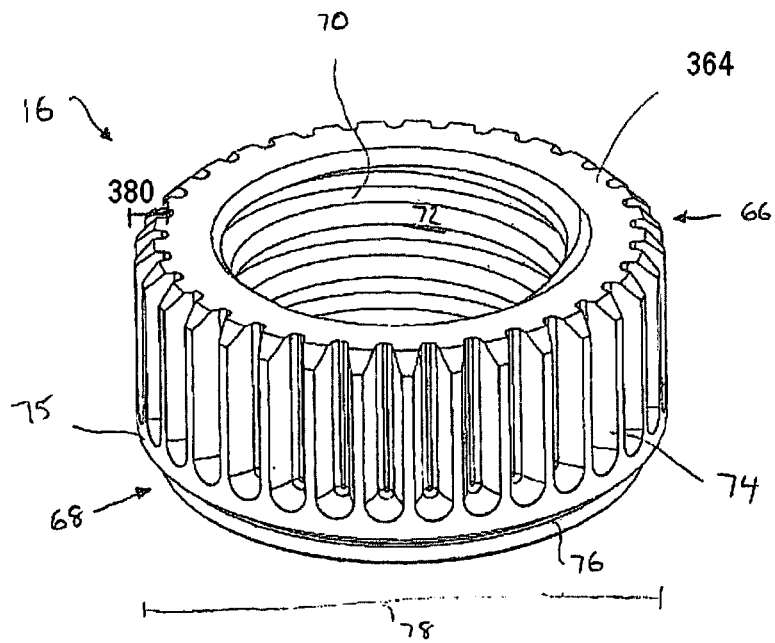
FIG. 6 is an elevated perspective view of one embodiment of a gear member of the implant of FIG. 1.
Figure 7:
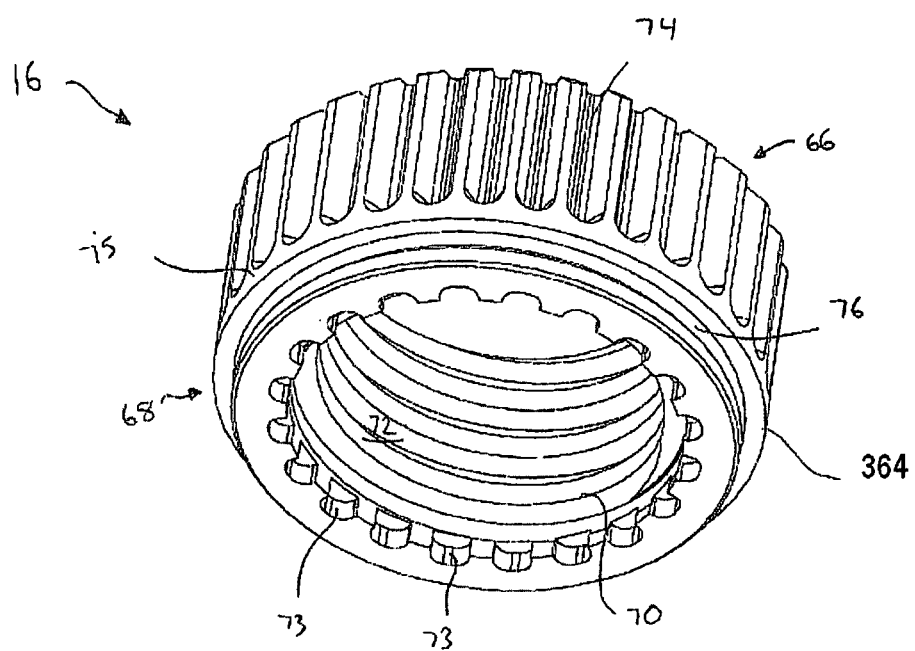
FIG. 7 is a bottom perspective view of the gear member of FIG. 6.

Referring now to FIGS. 6-7, a gear member 16 comprises a generally hollow body 364 extending from a distal end 66 to a proximal end 68 with a helical thread 70 along at least part of an inner wall 72 and an array of gear teeth 74 along a portion of the exterior wall 75. The gear member 16 is generally configured to rotatably connect to the distal end 42 of the outer member 14 and the internal helical thread 70 is configured to engage the external threads 32 of the inner member 12 to cause translation of the inner member 12 with respect to the outer member 14. In a preferred embodiment, the gear member 16 includes a cylindrical cutout feature 76 extending around the inner wall to cooperatively receive the lip 54 of the outer member 14. In this regard, the gear member 16 may rotate freely with respect to the outer member 14 while being retained from longitudinal and lateral movement. In a preferred embodiment, the gear member 16 also includes a series of cutouts 73 located proximate to the proximal end 68 for engaging a portion of a locking member.

With continued reference to FIGS. 6-7, the gear teeth 74 extend substantially from the proximal end 68 to the distal end 66 and extend around the entire periphery of at least a portion of the exterior wall 75. The outer-most external diameter 78 of the gear member 16 is sized to be the same as or slightly smaller than the smallest outer diameter of the endplates 20, 62 and the outer member 14. In this regard, when the implant 10 is viewed from the end in a plane perpendicular to the longitudinal axis 18, the gear member 16 does not protrude radially outward from beyond the perimeter of the endplates 20, 62.

As shown in FIG. 7, in a preferred embodiment, the gear teeth 74 extend a width 380 in a generally radial direction and generally extend radially outward to the outer diameter of the gear member 16. In this regard, the teeth 74 may be designed to have a width 380 to accommodate the expected gear forces given the particular gear ratio, types of material used, and desired overall diameter of prosthetic device 10. One skilled in the art will appreciate that the larger the outer diameter to which the teeth 74 radially extend, the larger the teeth 74 may be designed while still maintaining the same gear ratio. In this regard, when the teeth 74 are made larger, they generally have a better mechanical strength. Also, the ability to design larger, wider, and stronger teeth 74 is advantageous for embodiments where the implant 10 is made of PEEK, other plastic, or other non-metallic materials that may have less mechanical strength than, for instance, titanium.

Furthermore, as described in one embodiment, because the outer-most diameter of the gear member 16 may be as large as the outer diameter of the endplates 20, 62, and the teeth 74 extend radially to the outer-most diameter of the gear member 16, a larger inner diameter of the gear member 16 may be manufactured without compromising mechanical gear strength. As a result, a larger overall inner diameter of the implant 10 may be accommodated which allows the packing of more bone material therein and facilitates bone fusion once the implant 10 is implanted.

Figure 3:
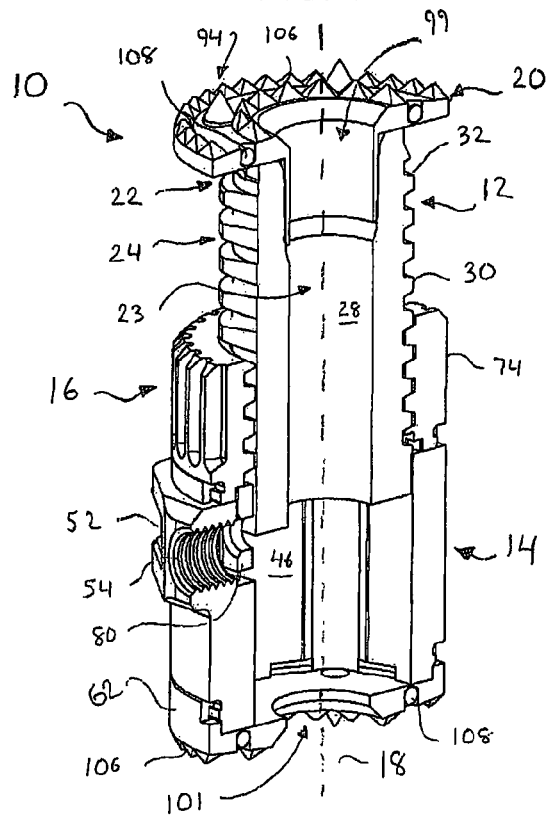
FIG. 3 is a cross-sectional view of the implant of FIG. 1 taken along line 3-3 of FIG. 1.
Figure 2:
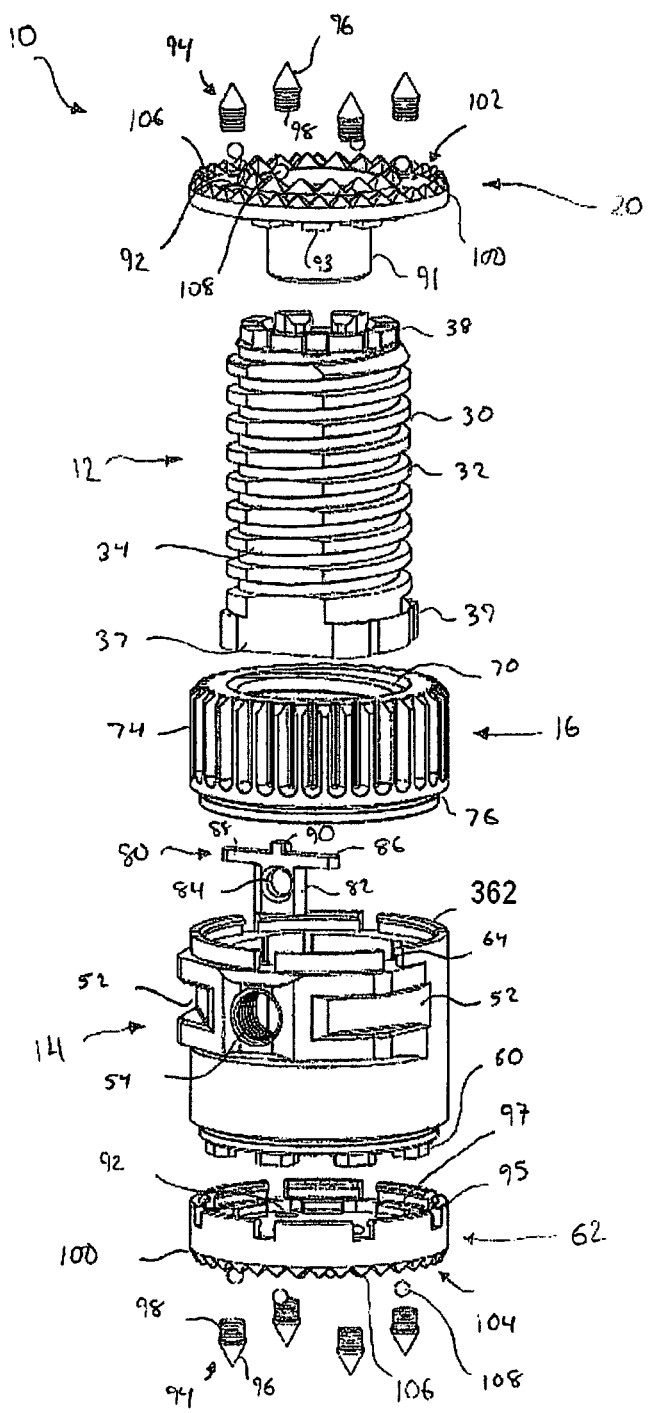
FIG. 2 is an exploded view of the implant of FIG. 1.
Figure 4:
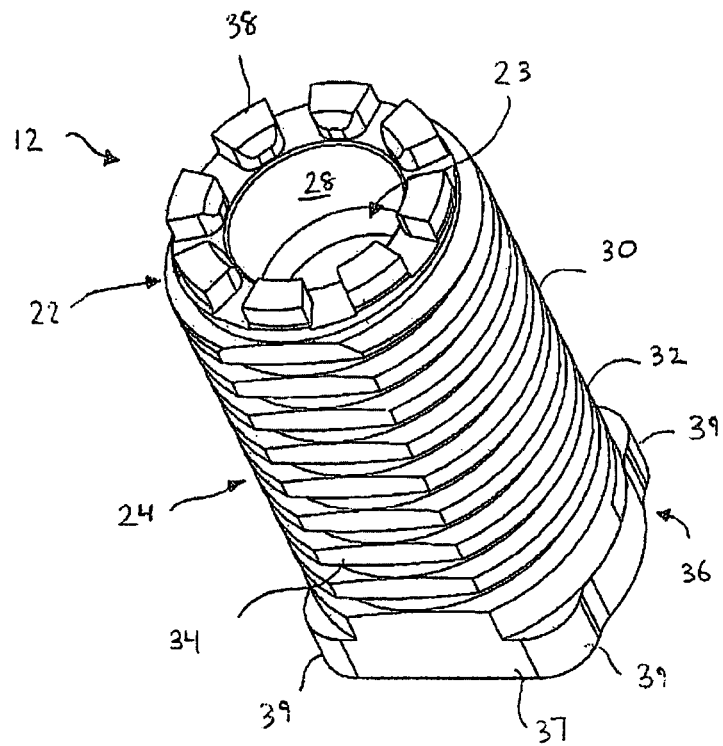
FIG. 4 is perspective view of an embodiment of an inner member of the implant of FIG. 1.

As seen in FIGS. 1-3, in a preferred embodiment, the teeth 74 are exposed to the exterior of prosthetic device 10. Because the teeth 74 are exposed around the periphery, little to no material is needed to cover up the exposed teeth, which generally makes the implant 10 lighter and easier to manufacture than prior art devices that require covering the gear teeth. In addition, the gear member 16 is more easily visible by a surgeon and more readily accessible by a rotation tool than devices that hide or cover gear teeth.

Referring to FIGS. 2, 5, and 7, in a preferred embodiment, the implant 10 also includes a locking member 80. The locking member 80 may be provided to substantially restrict all relative movement between inner member 12 and outer member 14, when, for example, the desired expansion of the prosthetic device 10 has been obtained. The locking member 80 has a body portion 82 with a through-hole 84. In a preferred embodiment, the body portion 82 has at least one, but preferably two, outwardly extending, flexible arms 86, 88 and at least one engagement member 90. In other preferred embodiments, instead of flexible arms 86, 88, it is contemplated that the locking member 80 may include an alternate biasing member, such as a leaf spring. The locking member 80 is configured and dimensioned to be received in the channel 57 of the outer member 14 in such a manner that the arms 86,88 rest against a shelf portion in the channel 57 and the through-hole 84 partially aligns with opening 54. The engagement member 90 preferably protrudes upwardly and is configured and dimensioned to engage the cutouts 73 of the gear member 16 to prevent the gear member 16 from rotating.

Referring now to FIGS. 1-3, in a preferred embodiment, the endplates 20, 62 are shown wherein the endplate 20 connects to the inner member 12 and endplate 62 connects to the outer member 14. In a preferred embodiment, endplate 20 includes an extension portion 91 which is received in the interior portion 23 of inner member 12, for example, in an interference or snap fit and includes a plurality of tabs 93 which interdigitate with tabs 38 to connect and position endplate 20 with respect to the inner member 12. Endplate 62 includes an extension portion 95 which engages the proximal end 44 of the outer member 14, for example, in an interference or snap fit and includes a plurality of tabs 97 which interdigitate with tabs 60 to connect and position endplate 62 with respect to the outer member 14. The endplates 20, 62 also preferably include hollow interior portions 99, 101 which are in fluid communication with the hollow interior portions 23, 50 of inner member 12 and outer member 14, respectively.

In a preferred embodiment, each endplate 20, 62 is generally annular in shape when viewed from the end or perpendicular to the longitudinal axis 18. It is, however, contemplated that the endplates 20, 62 can be other shapes including oblong, elliptical, kidney bean, polygonal, or geometric. Preferably, the endplates 20, 62 are designed to resemble or mimic the footprint of the vertebral body to which the endplates will engage. In this regard, endplates 20, 62 are configured to engage portions of the vertebrae in a predetermined orientation to maximize contact of the superior surface of the endplates 20, 62 with bone.

The dimensions of endplates 20, 62 can be varied to accommodate a patient's anatomy. In some embodiments, the endplates 20, 62 have a wedge-shaped profile to accommodate the natural curvature of the spine. In anatomical terms, the natural curvature of the lumbar spine is referred to as lordosis. When implant 10 is to be used in the lumbar region, the angle formed by the wedge should be approximately between 3.5 degrees and 16 degrees so that the wedge shape is a lordotic shape which mimics the anatomy of the lumbar spine. In alternate embodiments, the wedge shape profile may result from a gradual increase in height from an anterior side to a posterior side to mimic the natural curvature, kyphosis, in other regions of the spine. Thus, in other embodiments, the angle may be between about −4 degrees and −16 degrees.

As shown in FIGS. 1-3, in a preferred embodiment, the endplates 20, 40 include a plurality of mounting holes 92 spaced around the perimeter of each endplate 20, 40 for receiving insertable bone engaging members 94. In one embodiment, bone engaging members 94, comprise conical spikes 96 each having a cylindrical base portion 98 configured to fit within holes 92, for instance, by press-fit or by threaded engagement. In alternate embodiments, differently shaped bone engaging members 100 may be used, or in other embodiments no bone engaging members may be used. Referring again to FIG. 2, according to one embodiment, endplates 20, 62 have chamfered edges 100 around the perimeter to facilitate insertion and/or accommodate the shape of the vertebral bodies which they engage. The superior or bone engaging surfaces 102, 104 of endplates 20, 62 may also include numerous types of texturing to provide better initial stability and/or grasping contact between the end plate and the respective vertebrae. In a preferred embodiment, the texturing is a plurality of teeth 106. In preferred embodiments where the implant 10 is manufactured from PEEK or other plastic materials, the endplates 20, 62 may also include radio-opaque material, such as tantalum markers 108, which aid in providing location markers in radiographic images.

In preferred embodiments, the length, diameter, and shape of prosthetic device 10 may vary to accommodate different applications, different procedures, implantation into different regions of the spine, or size of vertebral body or bodies being replaced or repaired. For example, implant 10 may be expandable to a longer distance to replace multiple vertebral bodies. Also endplates 20, 62 can be sized and shaped as well as positioned to accommodate different procedures and approached to the spine. For example, endplates 20, 62 may be made smaller for smaller statured patients or for smaller regions of the cervical spine. In addition, it is not required that endplates 20, 62 be shaped and sized identically and in alternate embodiments they can be shaped or sized differently than each other and/or include different bone engaging members or texturing.

Figure 8:
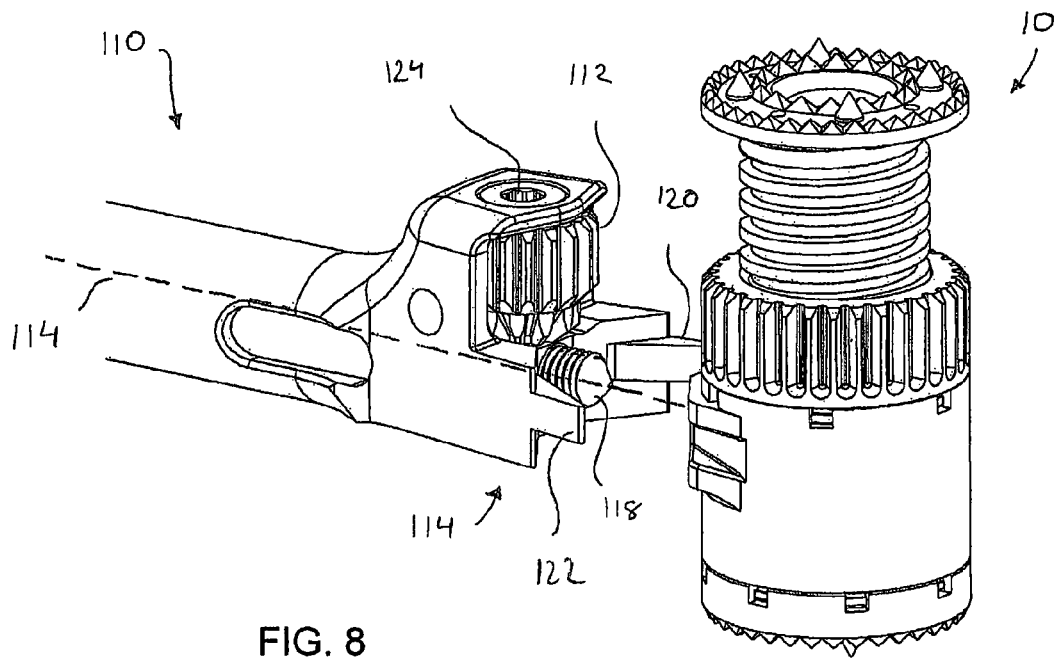
FIG. 8 is a perspective of one embodiment of a tool according to the present invention.
Figure 9:
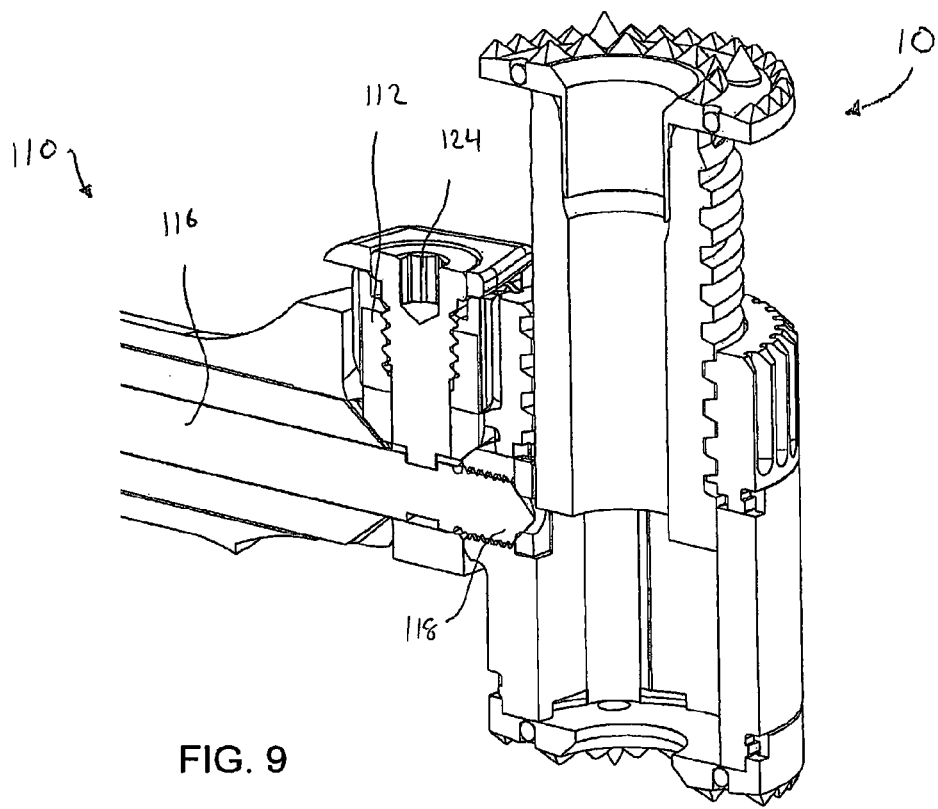
FIG. 9 is a cross-sectional view of the tool of FIG. 8 shown engaging an embodiment of an expandable implant according to the present invention.
Figure 10:
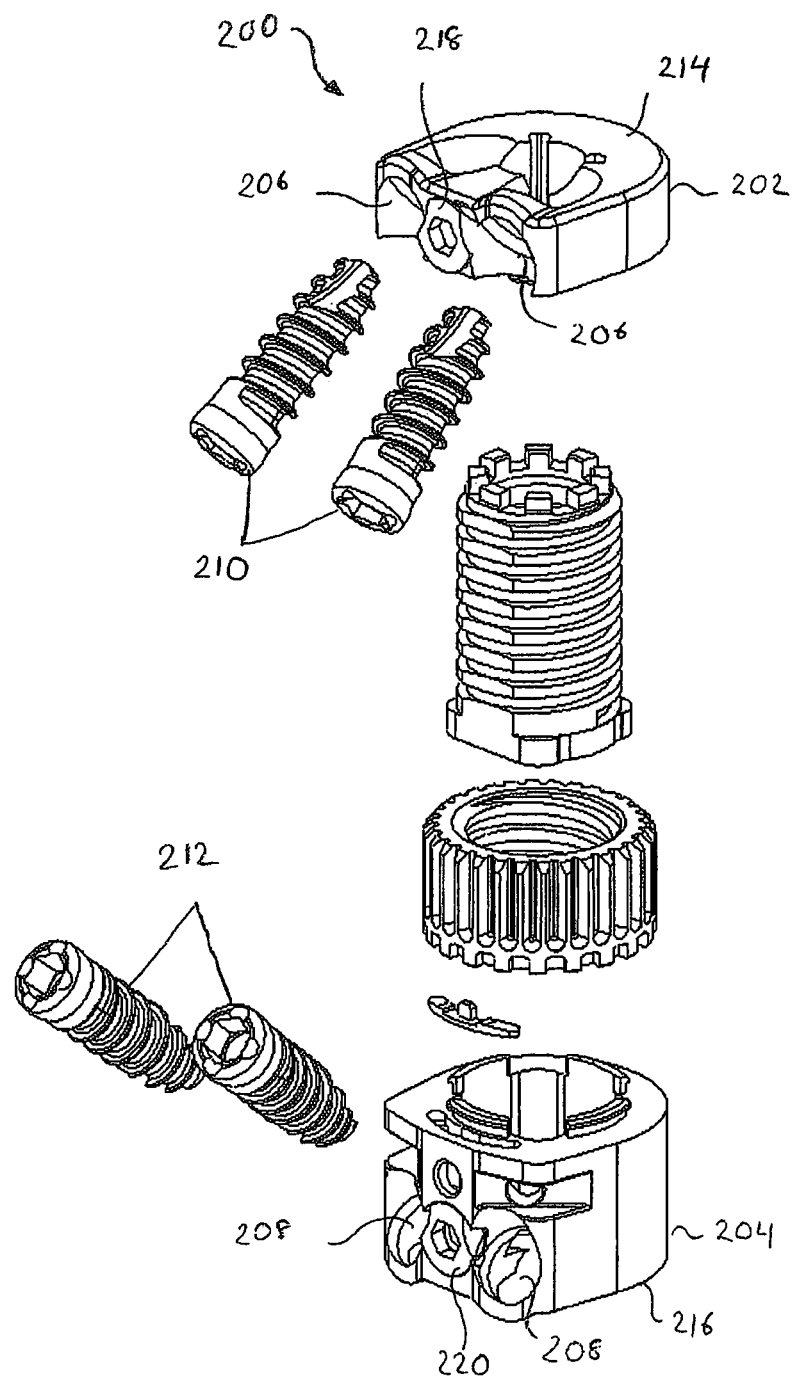
FIG. 10 is a perspective view of another embodiment of an implant according to the present invention.

Turning now to FIGS. 8-9, the implant 10 may be expanded by a tool 110 that includes a gear member 112 at its distal end 114. The tool 110 extends along a tool axis 114 and in operation the tool 110 is configured to engage the implant 10 such that the tool axis 114 is generally perpendicular to the longitudinal axis 18. The gear member 112 is configured to engage teeth 74 of the gear member 16 such that when the gear member 112 is rotated about the axis of the tool 110, the gear member 16 of the implant 10 is rotated about the longitudinal axis 18 and the inner member 12 translates along the longitudinal axis 18 to either expand or contract the implant 10. In a preferred embodiment, the tool 110 may include a central shaft 116 having a threaded distal tip portion 118 that extends distally beyond gear member 112 to facilitate location and mounting of tool 110 with the implant 10. The threaded distal tip portion 118 preferably includes a generally conical end portion and may be configured to extend radially through the opening 54 and threadably engage opening 54 in the outer member 14.

With continued reference to FIGS. 8-9, in one embodiment of prosthetic device 10 at least one, but preferably a plurality of mounting features or slots 52 are provided along the outer surface 48 of outer member 14. The tool 110 includes at least one, but preferably two, articulating arms 120, 122 that engage slots 52 for better engagement of the tool 110 with the implant 10 during insertion of the implant 10. In another preferred embodiment, the tool 110 may include arms 120, 122 that do not articulate.

In an exemplary use of the tool 110 with the implant 10, the tool 110 initially engages the slots 52 of the implant 10 via the arms 120, 122 and gear member 112 engages gear member 16 via their respective interdigitating teeth. A control member on the proximal end of the tool 110 (not shown) is manipulated to advance the central shaft 116 toward opening 54. The threaded tip portion 118 enters into opening 54 engaging the threads in opening 54 as well as engaging the through-hole 84 of locking member 80. It is also contemplated that the central shaft 116 is not movable with respect to the tool 110. In that embodiment, the entire tool 110 is moved so that the central shaft can enter and engage the opening 54 and the through-hole 84. As discussed earlier, the though-hole 84 is offset from opening 54, thus, when threaded tip 118 engages and advances into the opening 54 and the through-hole 84, the locking member 80 is pulled downwardly, riding along the conical edge of the tip 118 until the through-hole 84 is aligned with the opening 54. As the locking member 80 is pulled downwardly, the arms 82, 84 are flexed and the engagement member 90 disengages from the cutout 73 of the gear member 16 allowing the gear member 16 to rotate freely. The gear member 112 of tool 110 is then rotated via opening 114 which, in turn, rotates gear member 16. As discussed above, the rotation of gear member 16 results in the movement of inner member 12 causing the implant 10 to either expand or contract, depending on the direction the gear member 16 is rotated. Once the desired height for implant 10 is achieved, the tool member 110 is disengaged from implant 10. When the tool 110 is removed, the locking member 80 returns to the back to its initial position because of the arms 82, 84 returning back to their unflexed, at-rest state. The initial position of locking member 80 prevents the gear member 16 from turning because of the engagement of engagement member 90 with the cutouts 73. In that regard, implant 10 is locked from movement when the locking member 80 is in its initial position.

The benefit provided by the present locking mechanism is that it allows for a positive lock that engages and disengages automatically with the engagement and disengagement of the tool 110 with the implant 10, which minimizes the steps the surgeon must perform during the procedure.

Referring now to FIGS. 10-13, alternate preferred embodiments of endplates for the expandable implant 10 are shown. Looking at FIG. 10, in one variation, the endplates 202 and outer member 204 each include at least one screw hole 206, 208, but, preferably, each include two screw holes. The screw holes 206, 208 are configured and dimensioned to receive screws 210, 212. In a preferred embodiment, the screw holes 206, 208 are angled such that when the screws 210, 212 are seated in the screw holes 206, 208, the screws 210, 212 will extend outwardly from the superior surface 214 of endplate 202 and inferior surface 216 of outer member 204. Endplate 202 and outer member 204 also preferably include a locking element 218, 220 which, in a first position, allow the screws 210, 212 to back out from the seated position and, in a second position, block the screws 210, 212 from backing out of the seated position. In an exemplary use, once the implant 200 is installed and expanded to the desired position, the screws 210, 212 can be installed through the screw holes 206, 208 in such a manner as to purchase into the adjacent vertebral bodies. Once the screws 210, 212 are properly installed, including being engaged with the adjacent vertebral bodies, the locking elements 218, 220 can be actuated to block the screws 210, 212 from backing out of their installed position. The inclusion of screws 210, 212 in the endplate 202 and the outer member 204 provides for additional fixation of the implant 200 in the intervertebral space.

Figure 11:
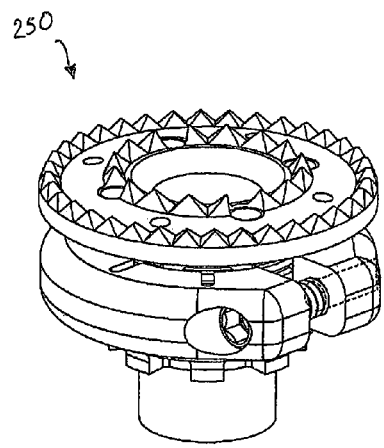
FIG. 11 is a perspective view of another embodiment of an endplate of an implant according to the present invention.
Figure 12:
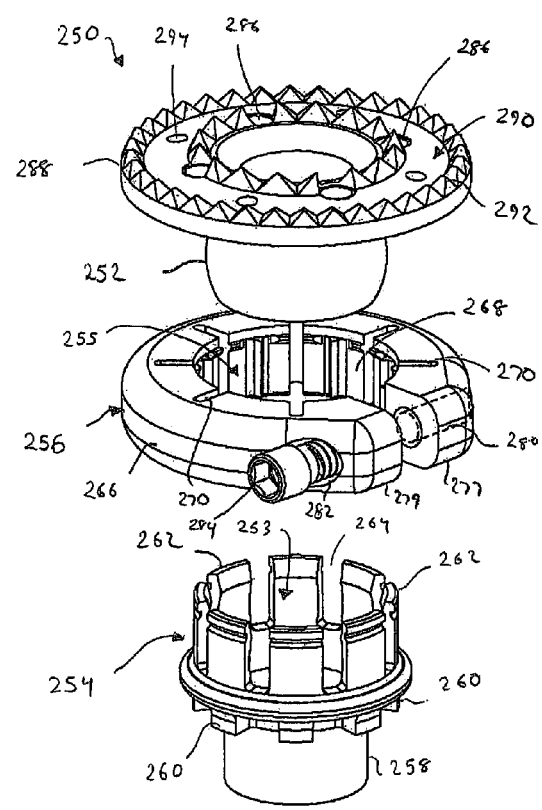
FIG. 12 is an exploded view of the endplate of FIG. 11.
Figure 13:
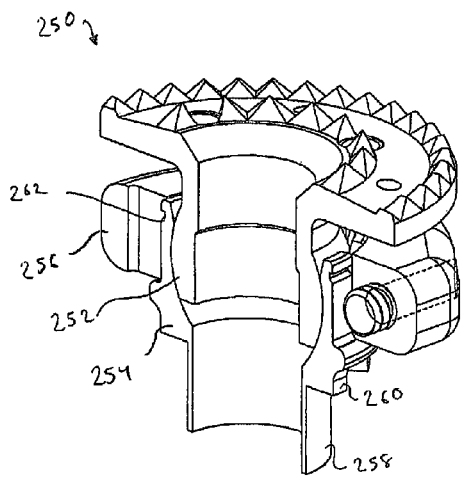
FIG. 13 is a cross-sectional view of the endplate of FIG. 11.

Turning to FIGS. 11-13, another preferred embodiment of an endplate 250 is shown. The endplate 250 is similar to endplate 20 but includes the additional functionality of being poly-axially rotatable with respect to an implant. In a preferred embodiment, endplate 250 includes a generally arcuate extension portion 252 which is received in an interior portion 253 of a receiving member 254 in such a manner as to allow the endplate 250 to move poly-axially with respect to the receiving member 254.

In a preferred embodiment, the receiving member 254 is received in an interior portion 255 of a locking ring 256. The receiving member 254 preferably includes a neck portion 258 as well as a plurality of tabs 260. The neck portion 258 is configured and dimensioned to be received within a hollow interior of an inner member, for example, in an interference or snap fit, and the plurality of tabs 260 interdigitate with tabs to connect and position the receiving member 254 with respect to an inner member. The receiving member 254 further includes a plurality of fingers 262 configured to cooperatively receive the extension portion 252 of endplate 250. A plurality of relief spaces or slots 264 are radially spaced between fingers 262 to allow fingers 262 to bend or flex radially.

In a preferred embodiment, the locking ring 256 has a generally annular, c-shape and includes an exterior wall 266, an interior wall 268, and ends 277, 279. The interior wall 268 preferably defines and interior portion 255. In a preferred embodiment, the interior wall 268 includes a plurality of channel 270 which are spaced radially along the locking ring 256. The channels 270 allow the locking ring 256 to bend or flex radially. The ends 277, 279 each include openings 280, 282 which may be partially threaded. A locking element 284 is configured and dimensioned to be threadingly received in the openings 280, 282. It also contemplated that that locking element 284 can engage the ends 277, 279 by other non-threaded means, such as a sliding fit.

With continued reference to FIGS. 11-13, in a preferred embodiment, the endplate 250 includes a plurality of mounting holes 286 spaced around the perimeter of the endplate 250 for receiving insertable bone engaging members. In one embodiment, bone engaging members, comprise conical spikes each having a cylindrical base portion configured to fit within holes 286, for instance, by press-fit or by threaded engagement. In alternate embodiments, differently shaped bone engaging members may be used, or in other embodiments no bone engaging members may be used. According to one preferred embodiment, endplate 250 has chamfered edges 288 around the perimeter to facilitate insertion and/or accommodate the shape of the vertebral bodies which they engage. The superior or bone engaging surfaces 290 of endplate 250 may also include numerous types of texturing to provide better initial stability and/or grasping contact between the end plate and the respective vertebrae. In a preferred embodiment, the texturing is a plurality of teeth 292. In preferred embodiments where the implant is manufactured from PEEK or other plastic materials, the endplate 250 may also include radio-opaque material, such as tantalum markers 294, which aid in providing location markers in radiographic images.

In an exemplary use, during the implant installation and expansion to the desired position, the endplate 250 can move in poly-axial fashion with respect to the implant to accommodate the anatomy of the adjacent vertebral body as well as accommodate the natural curvature of the spine, such as kyphosis and lordosis. More specifically, the arcuate extension portion 252 is free to move in the interior portion 253 of the receiving portion 254. The fingers 262 are generally compliant and can flex to accommodate the movement of the arcuate extension portion 252. Once the desired positioning of the endplate 250 is achieved, the endplate 250 can be locked in place. The endplate 250 is locked in place by actuating the locking element 284. As the element 284 engages the threading in opening 280,282 the ends 277, 279 of the locking ring 256 are brought closer together contracting the ring 254 and reducing the size of the interior portion 255. As the ring 254 contracts, the fingers 262 of the receiving member 254, abutting against the inner wall 268, are flexed radially inwardly pushing against the extension portion 252. As a result, the endplate 250 is locked in place.

While the invention herein disclosed has been described by means of specific embodiments and applications thereof, numerous modifications and variations can be made thereto by those skilled in the art without departing from the scope of the invention as set forth in the claims.

What is claimed is:

1. An expandable prosthetic implant for engagement between vertebrae, comprising:
    an inner member having a hollow interior portion and an external portion and including a first end portion, the inner member being centered along a first longitudinal axis, the first end portion comprising a first screw hole and a second screw hole;
    a first screw configured and dimensioned to be received in the first screw hole and a second screw configured and dimensioned to be received in the second screw hole, the first and second screws capable of engaging a first vertebral body;
    a first blocking member having a second longitudinal axis positioned transverse to the first longitudinal axis, the first blocking member being rotatable about the second longitudinal axis from a first position to a second position,
    an outer member having a hollow interior portion configured to coaxially receive the inner member therein and including a second end portion, the second end portion comprising a third screw hole and a fourth screw hole;
    a third screw configured and dimensioned to be received in the third screw hole and a fourth screw configured and dimensioned to be received in the fourth screw hole, the third and fourth screws capable of engaging a second vertebral body;
    a gear member positioned coaxial to the inner member and outer member and axially fixed to the outer member, the gear member includes a helical thread along at least part of an inner wall and an array of gear teeth along a portion of an exterior wall, the gear teeth extending from a proximal end of the gear member to a distal end of the gear member; and
    a locking member configured to restrict relative movement between the inner member and the outer member, wherein the locking member is configured to be received in the outer member, wherein the locking member includes an engagement member that engages the gear member to prevent rotation of the gear member, and wherein said engagement member is an upwardly protruding engagement member configured to be received in a cutout in the gear member;
    wherein the inner and outer members are moveable relative to each other along the first longitudinal axis,
    wherein the locking member includes a through hole for receiving a tool to move the locking member relative to the gear member in a direction parallel to the first longitudinal axis.

2. The implant of claim 1, wherein the first screw hole is angled such that the first screw when received in the first screw hole will extend outwardly from an upper surface of the first end portion.

3. The implant of claim 1, wherein the gear teeth extend around a perimeter of the gear member.

4. The implant of claim 1, wherein the second screw hole is angled such that the second screw when received in the second screw hole will extend outwardly from an upper surface of the first end portion.

5. The implant of claim 1, wherein the second end portion further comprises a second blocking element for preventing the third and fourth screws from backing out once the third and fourth screws are in a seated position in the third and fourth screw holes.

6. The implant of claim 1, wherein the engagement member engages a cutout formed in the gear member to prevent rotation of the gear member.

7. The implant of claim 1, wherein the inner member includes a flattened portion and the outer member includes a flattened portion, wherein each of the flattened portions cooperate to prevent rotational movement of the inner member with respect to the outer member.

8. The implant of claim 1, wherein the inner member includes a base portion having at least one lobe and the outer member includes at least one depression, the lobes and depression cooperate to prevent rotational movement of the inner member with respect to the outer member.

9. The implant of claim 1, wherein the first blocking member is positioned between the first and second screw holes.

10. The implant of claim 1, wherein the first blocking member has a face and, when in the second position, a first portion of the face blocks the first screw hole and a second portion of the face blocks the second screw hole.

11. An expandable prosthetic implant for engagement between vertebrae, comprising:
    an inner member having a hollow interior portion and an external portion and including a first end portion, the inner member being centered along a first longitudinal axis, the first end portion comprising a first screw hole and a second screw hole;
    a first screw configured and dimensioned to be received in the first screw hole, the first bone screw capable of engaging a first vertebral body;
    a second screw configured and dimensioned to be received in the second screw hole, the second bone screw capable of engaging the first vertebral body;
    a first blocking member having a second longitudinal axis positioned transverse to the first longitudinal axis, the first blocking member being rotatable about the second longitudinal axis from a first position to a second position,
    an outer member having a hollow interior portion configured to coaxially receive the inner member therein and including a second end portion configured to engage a second vertebral body, wherein the inner and outer members are moveable relative to each other along the first longitudinal axis;

a gear member positioned coaxial to the inner member and outer member and axially fixed to the outer member, the gear member includes a helical thread along at least part of an inner wall and an array of gear teeth along a portion of an exterior wall, the gear teeth extending from a proximal end of the gear member to a distal end of the gear member; and a locking member configured to restrict relative movement between the inner member and the outer member, wherein the locking member is configured to be received in the outer member, wherein the locking member comprises a flexible body, and wherein the locking member includes an upwardly protruding engagement member configured to be received in a cutout in the gear member, wherein the locking member includes a through hole for receiving a tool to move the locking member relative to the gear member in a direction parallel to the first longitudinal axis.

12. The implant of claim 11, wherein at least a portion of the implant is formed of PEEK.

13. The implant of claim 11, wherein the second end portion comprises a third screw hole.

14. The implant of claim 13, further comprising a third bone screw configured and dimensioned to be received in the third screw hole, the third bone screw capable of engaging the second vertebral body.

15. The implant of claim 11, wherein the locking member is configured to be received in a channel formed within the outer member.

16. The implant of claim 11, wherein the locking member is configured to engage cutouts formed in the gear member.

17. An expandable prosthetic implant for engagement between vertebrae, comprising:

an inner member having a hollow interior portion and an external portion and including a first end portion configured to engage a first vertebral body;

an outer member having a hollow interior portion configured to coaxially receive the inner member therein and including a second end portion, the second end portion comprising a first screw hole and a second screw hole, wherein the outer member includes an opening configured and dimensioned to receive a portion of an implantation tool, wherein the inner and outer members are moveable relative to each other along a first longitudinal axis;

a first screw configured and dimensioned to be received in the first screw hole and a second screw configured and dimensioned to be received in the second screw hole, the first and second screws capable of engaging a second vertebral body;

a first blocking member having a second longitudinal axis positioned transverse to the first longitudinal axis, the first blocking member being rotatable about the second longitudinal axis from a first position to a second position, a gear member positioned coaxial to the inner member and outer member and axially fixed to the outer member, wherein the gear member includes a plurality of teeth along a portion of an exterior wall and a helical thread along at least part of an inner wall, the gear teeth extending from a proximal end of the gear member to a distal end of the gear member; and a locking member configured to restrict relative movement between the inner member and the outer member, wherein the locking member comprises a flexible body, and wherein the locking member includes an upwardly protruding engagement member configured to be received in a cutout in the gear member;

wherein the first end portion is a first endplate that is removably coupled to the inner member by a plurality of tabs, wherein the locking member includes a through hole for receiving a tool to move the locking member relative to the gear member in a direction parallel to the first longitudinal axis.

18. The implant of claim 17, wherein the first end portion comprises a third screw hole.

19. The implant of claim 18, further comprising a third screw configured and dimensioned to be received in the third screw hole, the third bone screw capable of engaging the first vertebral body.

* * * * *